United States Patent
Lu et al.

(10) Patent No.: US 7,071,365 B2
(45) Date of Patent: Jul. 4, 2006

(54) 3-ALKYLATED-5,5',6,6', 7, 7', 8, 8'—OCTAHYDRO-2, 2'-BINAPHTHOLS AND 3, 3'-DIALKYLATED- 5, 5', 6, 6', 7, 7', 8, 8'-OCTAHYDRO—2, 2'-BINAPHTHOLS AND PROCESSES FOR MAKING

(75) Inventors: Helen S. M. Lu, Wallingford, PA (US); Weiming Qiu, Wilmington, DE (US); Rafael Shapiro, Wilmington, DE (US)

(73) Assignee: Invista North America S.A.R.L., Wilmington, DE (US)

( * ) Notice: Subject to any disclaimer, the term of this patent is extended or adjusted under 35 U.S.C. 154(b) by 0 days.

(21) Appl. No.: 11/103,044

(22) Filed: Apr. 11, 2005

(65) Prior Publication Data

US 2005/0182279 A1 Aug. 18, 2005

Related U.S. Application Data

(60) Division of application No. 10/625,227, filed on Jul. 23, 2003, now abandoned, which is a continuation of application No. 09/994,099, filed on Nov. 26, 2001, now abandoned.

(51) Int. Cl.
*C07C 39/12* (2006.01)
(52) U.S. Cl. ..................................... 568/719
(58) Field of Classification Search ................ 568/719
See application file for complete search history.

(56) References Cited

U.S. PATENT DOCUMENTS

| | | | |
|---|---|---|---|
| 4,912,264 A | 3/1990 | Takeshita et al. | |
| 5,235,113 A | 8/1993 | Sato et al. | |
| 5,334,775 A * | 8/1994 | Gutierrez et al. | ........... 568/791 |
| 6,031,120 A | 2/2000 | Tam | |
| 6,069,267 A | 5/2000 | Tam | |
| 6,274,745 B1 | 8/2001 | Inanaga et al. | |
| 6,353,125 B1 | 3/2002 | Watchler et al. | |

FOREIGN PATENT DOCUMENTS

| | | |
|---|---|---|
| EP | 1038877 A1 | 9/2000 |
| JP | 07-252174 | 3/1995 |
| WO | WO99 06146 | 2/1999 |
| WO | WO99 36397 | 7/1999 |
| WO | WO99 62855 | 12/1999 |

OTHER PUBLICATIONS

Olah, G. A. *Friedel-Crafts and Related Reactions*, Wiley-Interscience: New York, 1964, vol. II, Part I, pp. v-vii.

Nilsson et al., 1970. *The Directing Effect of Annulated Rings in Aromatic Systems.*, ACTA Chemical Scandinavica vol. 24, pp. 580-588.

Findlay et al., 1971, *Applications of High-potential Quinones. Part IV. The Mechanism of Oxidation of 6-Hydroxytetralins.* J. W. A. Findlay and A. B. Turner, pp. 23-29.

Cram et al., J. Org. Chem. vol. 43, No. 10, 1978. *Host-Guest Complexation. 8.Macrocyclic Polyethers Shapted by Two Rigid Substituted Dinaphthyl or Ditertralyl Units*, pp. 1930-1946.

Roberts, R., *Friedel-Crafts Alkylation Chemistry*, Marcel Dekker, Inc., 1984, title pages only.

March, J., *Advanced Organic Chemistry*, 4th Edition, Wiley-Interscience: New York, 1992, pp. 534-539.

Kotsuki, Scandium (III) Trifluoromethanesulfonate-Catalyzed Friedel-Crafts Alkylation of Aromatic Compounds with Secondary Alcohol Methanesulfonates, Synlett, 1998, pp. 255-256.

Kotsuki, et al., 1999, New Convenient Friedel-Crafts Alkylation of Aromatic Compounds with Secondary Alcohol Methanesulfonates in the Presence of Scandium (III) Trifluoromethanesulfonate or Trifluoromethanesulfonic Acid as the Catalyst, Synthesis, No. 4, pp. 603-606.

Stillson et al., J. Am. Chem. Soc., 1945, The Hindered Phenols, 67, pp. 303-307.

Whitney Weinrich, Industrial and Engineering Chem., 1943, Vol. 35, pp. 264-272.

Tetrahedron Lett. 1997, 3,3'-Dinitro-octahydrobinaphthol: A New Chiral Ligand for Metal-Catalyzed Enantioselective Reactions, vol. 38, No. 33, pp. 5273-5276.

S. L. Aeilts et al., "A Readily Available and User-Friendly Chiral Catalyst for Efficient Enantioselective Olefin Metathesis", Angewandte Chemie. International Edition, Verlag Chemie. Weinheim, DE, vol. 40, No. 8, Apr. 17, 2001, pp. 1452-1456.

R. R. Schrock et al., "New Chiral Molybdenum Catalysts for Asymmetric Olefin Metathesis that Contain 3,3'-Disubstituted Octahydrobinaphtholate or 2,6-Dichlorophenylimido Ligands". Organometallics, vol. 21, No. 2, Jan. 21, 2002, pp. 409-417, XP002232616.

International Search Report, PCT/US02/37305.

* cited by examiner

*Primary Examiner*—Porfirio Nazario-Gonzalez

(57) ABSTRACT

The compositions 3-alkylated-5,5',6,6',7,7',8,8'-octahydro-2, 2'-binaphthol and 3,3'-dialkylated-5,5',6,6',7,7',8,8'-octahydro-2,2'-binaphthol are disclosed, as well as various processes for making them, all involving the alkylation of 5,5',6,6',7,7',8,8'-octahydro-2,2'-binaphthol.

6 Claims, No Drawings

3-ALKYLATED-5,5',6,6', 7, 7', 8, 8'—OCTAHYDRO-2, 2'-BINAPHTHOLS AND 3, 3'-DIALKYLATED- 5, 5', 6, 6', 7, 7', 8, 8'-OCTAHYDRO—2, 2'-BINAPHTHOLS AND PROCESSES FOR MAKING

CROSS-REFERENCE TO RELATED APPLICATIONS

This application is a divisional of application Ser. No. 10/625,227, filed Jul. 23, 2003, which was a continuation of application Ser. No. 09/994,099, filed Nov. 26, 2001.

FIELD OF THE INVENTION

This invention relates to the compositions 3-alkylated-5, 5',6,6',7,7',8,8'-octahydro-2,2'-binaphthols and certain 3,3'-dialkylated-5,5',6,6',7,7',8,8'-octahydro-2,2'-binaphthols and to processes for making 3-alkylated-, and 3,3'-dialkylated-5,5',6,6',7,7',8,8'-octahydro-2,2'-binaphthols, generally.

BACKGROUND OF THE INVENTION

Phosphorous-based ligands are useful as part of the catalyst system in industrially important reactions such as hydroformylation and hydrocyanation. The useful ligands include phosphines, phosphinites, phosphonites, and phosphites. See PCT patent applications WO 99/06146 and WO 99/62855. Both mono(phosphorous) ligands and bis(phosphorous) ligands are utilized in the art. Mono(phosphorous) ligands are compounds that contain a single phosphorus atom which serves as a donor to a transition metal, while bis(phosphorus) ligands, in general, contain two phosphorus donor atoms and typically form cyclic chelate structures with transition metals.

Processes for the preparation of 3,3'-dialkyl-5,5',6,6',7,7', 8,8'-octahydro-2,2'-binaphthols, unlike their 3-alkyl-5,5',6,6',7,7',8,8'-octahydro-2,2'-binaphthol analogs, appear in the literature. One such process, disclosed in J. Chem. Soc., C 1971, 23, teaches the preparation of 3,3'-di-t-butyl-5,5',6,6',7,7'8,8'-octahydro-2,2'-binaphthols by the coupling of 3-t-butyl-5,6,7,8-tetrahydro-2-naphthol using potassium ferricyanide and FeCl$_3$-based methods with yields of only 25% and 6%, respectively. Also disclosed is the coupling of 3-t-butyl-5,6,7,8-tetrahydro-2-naphthol to give 3,3'-di-t-butyl-5,5',6,6',7,7',8,8'-octahydro-2,2'-binaphthol can be carried out with a large excess MnO2 (20 times in weight).

Another process, disclosed in Acta Chem. Scand. 1970, 24, 580, teaches the coupling of 3,4-dimethyl-5,6,7,8-tetrahydro-2-naphthol to give 3,3',4,4'-tetramethyl-5,5',6,6',7, 7',8,8'-octahydro-2,2'-binaphthol with 43% yield. J. Org. Chem. 1978, 43, 1930 discloses the preparation of 3,3'-dimethyl-5,5',6,6',7,7',8,8'-octahydro-2,2'-binaphthol by LiAlH$_4$ reduction of 3,3'-di(bromomethyl)-5,5',6,6',7,7',8,8'-octahydro-2,2'-binaphthol.

There has been no report in the prior art regarding acid catalyzed alkylation of 5,5',6,6',7,7',8,8'-octahydro-2,2'-binaphthol to produce 3-alkyl-5,5',6,6',7,7',8,8'-octahydro-2, 2'-binaphthols or 3,3'-dialkyl-5,5',6,6',7,7'8,8'-octahydro-2, 2'-binaphthols. Acid catalyzed alkylation of phenols is known. For example, U.S. Pat. No. 4,912,264 discloses heteropoly acid catalyzed phenol and naphthol alkylation. U.S. Pat. No. 2,733,274 discloses cresol sulfonic acid catalyzed phenol alkylation. J. Am. Chem. Soc., 1945, 67, 303 discloses aluminum chloride catalyzed phenol alkylation. Industrial and Engineering Chem., 1943, 35, 264 discloses sulfuric acid catalyzed phenol alkylation. Friedel-Crafts alkylation of aromatic compounds has also been reviewed. For example, see Olah, G. A. *Friedel-Crafts and Related Reactions*, Wiley-Interscience: New York, 1964, Vol. II, part I, Roberts, R. *Friedel-Crafts Alkylation Chemistry*, Marcel Dekker, 1984, and March, J. *Advanced Organic Chemistry*, 4$^{th}$ Edition, Wiley-Interscience: New York, 1992, pp 534–539.

Recently, it was disclosed that rare earth metal trifluoromethanesulfonates as water-tolerant Lewis acid catalysts can be utilized in Friedel-Crafts alkylation of benzene and phenol derivatives with secondary alkyl methanesulfonates. See SynLett, 1998, 255–256 and Synthesis, 1999, 603–606.

It is not practical to use LiAlH$_4$, a large excess of MnO$_2$, or even a stoichiometric amount of potassium ferricyanide to carry out industrial scale preparations of alkylated, hydrogenated binaphthols. Such a process would be expected to generate a large amount of byproducts. Therefore, a need exists in the art for a practical and general method to prepare 3-alkylated-5,5',6,6',7,7',8,8'-octahydro-2,2'-binaphthols and 3,3'-dialkylated-5,5',6,6',7,7',8,8'-octahydro-2,2'-binaphthols.

SUMMARY OF THE INVENTION

In its composition of matter aspect, the present invention provides 3-alkylated-5,5',6,6',7,7',8,8'-octahydro-2,2'-binaphthols of the formula (1) and 3,3'-dialkylated-5,5',6,6',7, 7',8,8'-octahydro-2,2'-binaphthols of the formula (2).

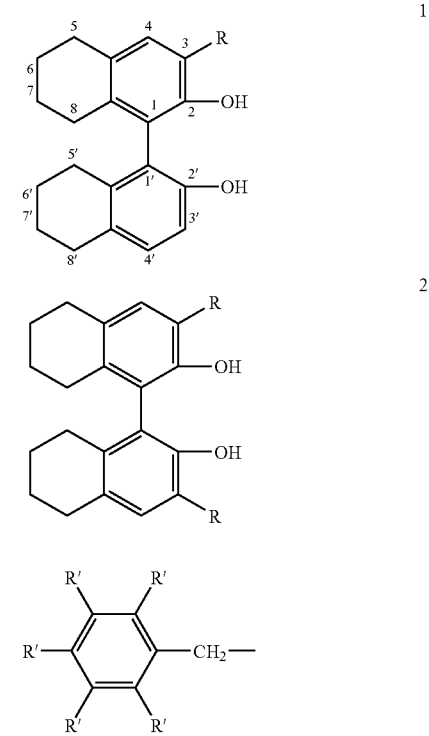

wherein:

R is C$_1$ to C$_{20}$ alkyl, C$_3$ to C$_{20}$ cycloalkyl, or benzyl of the formula wherein each R' is independently H, alkyl or cycloalkyl of up to 6 carbons; provided that in formula (2), when R is alkyl, the alkyl must be other than methyl or t-butyl.

In its first process aspect, the present invention provides a process for making 3-alkylated-5,5',6,6',7,7',8,8'-octahydro-2,2'-binaphthols and 3,3'-dialkylated-5,5',6,6',7,7',8,8'-octahydro-2,2'-binaphthols by contacting 5,5',6,6',7,7',8,8'-octahydro-2,2'-binaphthol with an alkene or cycloalkene in the presence of an acid catalyst such as aluminum chloride, trifluoromethanesulfonic acid, tosylic acid, phosphotungstic acid, silicotungstic acid, phosphomolybdic acid, zirconium or aluminum triflate, polymeric perfluorinated sulfonic acid (such as the DuPont material sold as Nafion®) and polymeric sulfonic acid (such as the material sold by Aldrich as Amberlyst® 15 ion-exchange resin or the material sold by Dow as Dowex 32®).

In its second process aspect, the present invention provides a process for making 3-alkylated-5,5',6,6',7,7',8,8'-octahydro-2,2'-binaphthols and 3,3'-dialkylated-5,5',6,6',7,7',8,8'-octahydro-2,2'-binaphthols by contacting 5,5',6,6',7,7',8,8'-octahydro-2,2'-binaphthol with benzyl halides or tertiary alkyl halides in the presence of a Lewis acid catalyst, such as aluminum chloride or zinc chloride.

In its third process aspect, the present invention provides a process for making 3-alkylated-5,5',6,6',7,7',8,8'-octahydro-2,2'-binaphthols and 3,3'-dialkylated-5,5',6,6',7,7',8,8'-octahydro-2,2'-binaphthols by contacting 5,5',6,6',7,7',8,8'-octahydro-2,2'-binaphthol with alkyl sulfonates, fluorinated alkyl sulfonates, alkyl benzenesulfonates, or alkyl p-toluenesulfonates in the presence of an acid catalyst such as trifluoromethanesulfonic acid or scandium triflate.

In its fourth process aspect, the present invention provides a process for making 3-alkylated-5,5',6,6',7,7',8,8'-octahydro-2,2'-binaphthols and 3,3'-dialkylated-5,5',6,6',7,7',8,8'-octahydro-2,2'-binaphthols by contacting 5,5',6,6',7,7',8,8'-octahydro-2,2'-binaphthol with benzyl alcohol, or secondary or tertiary alcohol in the presence of aluminum chloride, trifluoromethanesulfonic acid, tosylic acid, phosphotungstic acid, silicotungstic acid, phosphomolybdic acid, zirconium or aluminum triflate, polymeric perfluorinated sulfonic acid (such as Nafion®) or polymeric sulfonic acid.

In another aspect, the present invention is a compound of the formula

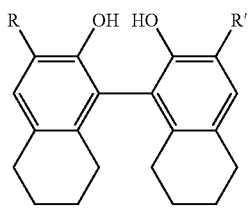

wherein:
R is H; and
R' is ethyl, $C_3$ to $C_6$ secondary, tertiary, or cyclic alkyl;
or a compound of the above formula wherein R and R' are the same and are selected from the group consisting of ethyl, $C_3$ to $C_6$ secondary or cyclic alkyl.

Preferred compounds are those wherein R and R' are the same are selected from the group consisting of ethyl, isopropyl, cyclopentyl, and cyclohexyl.

DETAILED DESCRIPTION OF THE INVENTION

The alkylated 5,5',6,6',7,7',8,8'-octahydro-2,2'-binaphthols of this invention may be prepared by alkylation of 5,5',6,6',7,7',8,8'-octahydro-2,2'-binaphthol in the presence of a catalyst, as shown below.

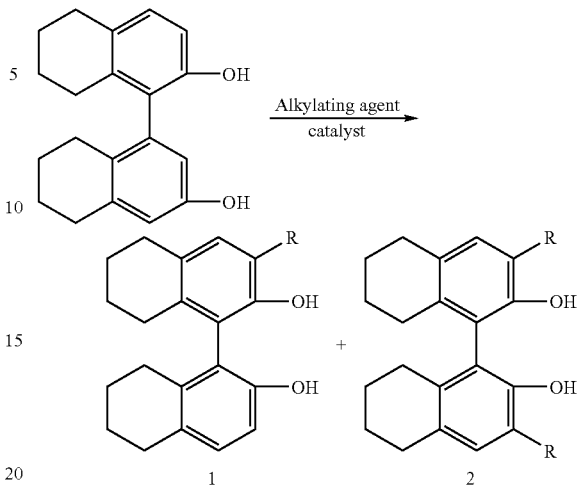

The starting material, 5,5',6,6',7,7',8,8'-octahydro-2,2'-binaphthol, can be obtained by the hydrogenation of 2,2'-binaphthol using a $PtO_2$ catalyst, as described in Tetrahedron Lett. 1997, 5273.

The first process aspect of the present invention is a process for making alkylated 5,5',6,6',7,7',8,8'-octahydro-2,2'-binaphthols by an acid-catalyzed, selective alkylation of 5,5',6,6',7,7',8,8'-octahydro-2,2'-binaphthol by alkenes or cycloalkenes in the presence of an acid catalyst. The acid catalyst may be a Lewis acid or a protic acid. Suitable catalysts include the following: $AlCl_3$, trifluoromethanesulfonic acid, tosylic acid, phosphotungstic acid, silicotungstic acid, phosphomolybdic acid, zirconium or aluminum triflate, polymeric perfluorinated sulfonic acid (such as the material sold by DuPont as Nafion®) and polymeric sulfonic acid (such as the material sold by Aldrich as Amberlyst® 15 ion-exchange resin or the material sold by Dow as Dowex 32®). Phosphotungstic acid is preferred. The alkenes include monoethylenically unsaturated compounds containing from 3 to 20 carbons, such as propylene, butene, pentene, hexene, cyclopentene, cyclohexene, etc. The reaction may be carried out at 20° C. to 220° C., preferably at 90° C. to 180° C., when mono-substituted or 1,2-disubstituted alkenes are utilized as alkylating reagents, and 40° C. to 90° C. when 1,1-disubstituted, tri-substituted, tetra-substituted or aryl-substituted alkenes are utilized as alkylating reagents. The alkylation reaction may be carried out neat (without solvent) or in inert solvents such as nitromethane, methylene chloride, dichloroethane, chlorobenzene, dichlorobenzene, nitrobenzene or a combination of these solvents. Other solvents such as benzene, toluene, and xylene may also be used, but the solvents may become alkylated. When the boiling point of the alkene is lower than the reaction temperature, the reaction may be carried out in an autoclave or by feeding the alkene at atmosphere pressure. The reaction may be carried out in an autoclave when the boiling point of the solvent(s) is lower than the reaction temperature. A large excess of alkene over binaphthol gives double alkylated 5,5',6,6',7,7',8,8'-octahydro-2,2'-binaphthol, while about two equivalents or less of alkene (relative to 5,5',6,6',7,7',8,8'-octahydro-2,2'-binaphthol) gives both mono and double alkylated 5,5',6,6',7,7',8,8'-octahydro-2,2'-binaphthols.

The second process aspect of the present invention is a process for making alkylated 5,5',6,6',7,7',8,8'-octahydro-2, 2'-binaphthol by the reaction of 5,5',6,6',7,7',8,8'-octahydro-2,2'-binaphthol with benzyl halide or tertiary alkyl halide in the presence of a Lewis acid catalyst. Suitable catalysts include the following: aluminum chloride, zinc chloride, boron trichloride, $SnCl_4$, $SbCl_5$, and $ZrCl_4$. Zinc chloride is preferred. Suitable halides are bromides and chlorides. The reaction may be carried out at 0° C. to 100° C., preferably at 20° C. to 80° C. The alkylation reaction may be carried out in inert solvents such as nitromethane, methylene chloride, dichloroethane, chlorobenzene, dichlorobenzene, nitrobenzene or a combination of these solvents. Other solvents such as benzene, toluene, and xylene may also be used, but the solvents may become alkylated. When tertiary alkyl halide is used as an alkylating reagent, the reaction is very selective towards mono-alkylated 5,5',6,6',7,7',8,8'-octahydro-2,2'-binaphthol even when several equivalents excess of tertiary alkyl halide are used. However, double alkylated 5,5',6,6',7,7',8,8'-octahydro-2,2'-binaphthol eventually is formed when a large excess of tertiary alkyl halide is used and the reaction is allowed to run at higher temperature and for longer time. When benzyl halide is used as an alkylating reagent, double benzylated 5,5',6,6',7,7',8,8'-octahydro-2,2'-binaphthol is formed when a large excess of benzyl halide relative to binaphthol is used, while one equivalent of the benzyl halide (relative to 5,5',6,6',7,7',8,8'-octahydro-2,2'-binaphthol) gives predominantly mono-benzylated 5,5',6,6',7,7',8,8'-octahydro-2,2'-binaphthols.

The third process aspect of the present invention is a process for making alkylated 5,5',6,6',7,7',8,8'-octahydro-2,2'-binaphthol by the reaction of 5,5',6,6',7,7',8,8'-octahydro-2,2'-binaphthol with alkyl sulfonates such as alkyl methanesulfonates, alkyl triflates, alkyl p-toluenesulfonates, and alkyl benzenesulfonates in the presence of an acid catalyst. Suitable alkyl sulfonates are of the formula $A-SO_3-B$, wherein A is $C_1$ to $C_8$ alkyl, $C_1$ to $C_8$ fluorinated alkyl, $C_6$ to $C_{10}$ aryl, or $C_6$ to $C_{10}$ fluorinated aryl; and B is $C_1$ to $C_{20}$ alkyl. Suitable catalysts for alkylation of 5,5',6,6',7,7',8,8'-octahydro-2,2'-binaphthol with alkyl sulfonates include Lewis acids such as aluminum chloride and boron trifluoride, as well as other acid catalysts such trifluoromethanesulfonic acid, tosylic acid, and rare earth metal triflates such as scandium trifluoromethanesulfonate, ytterbium trifluoromethanesulfonate, or lanthanum trifluoromethanesulfonate. Trifluoromethanesulfonic acid and scandium trifluoromethanesulfonate are the preferred catalysts. Alkylation of 5,5',6,6',7,7',8,8'-octahydro-2,2'-binaphthol may be carried out at 20° C. to 220° C., preferably at 90° C. to 180° C. The alkylation reaction may be carried out in inert solvents such as nitromethane, methylene chloride, carbon tetrachloride, dichloroethane, chlorobenzene, dichlorobenzene, nitrobenzene or a combination of these solvents. Other solvents such as benzene, toluene, and xylene may also be used, but the solvents may become alkylated. The product of the reaction of 5,5',6,6',7,7',8,8'-octahydro-2,2'-binaphthol with alkyl sulfonates varies depending on stoichometry and alkylation reagent used. A large excess of alkyl sulfonate gives double alkylated 5,5',6,6',7,7',8,8'-octahydro-2,2'-binaphthol, while about 1.5 equivalents or less of alkyl sulfonate (relative to 5,5',6,6',7,7',8,8'-octahydro-2,2'-binaphthol) gives predominately mono alkylated 5,5',6,6',7,7',8,8'-octahydro-2,2'-binaphthols.

The fourth process aspect of the present invention is a process for making alkylated 5,5',6,6',7,7',8,8'-octahydro-2,2'-binaphthol by the reaction of 5,5',6,6',7,7',8,8'-octahydro-2,2'-binaphthol with benzyl alcohol, secondary and tertiary alcohols containing 3 to 20 carbon atoms, in the presence of an acid catalyst. Suitable catalysts include the following: trifluoromethanesulfonic acid, tosylic acid, aluminum chloride, phosphotungstic acid, silicotungstic acid, phosphomolybdic acid, polymeric perfluorinated sulfonic acid (such as Nafion®) and polymeric sulfonic acid (such as Amberlyst®15 ion-exchange resin and Dowex 32®). Trifluoromethanesulfonic acid is preferred. Alkylation of 5,5',6,6',7,7',8,8'-octahydro-2,2'-binaphthol with alcohols may be carried out at 20° C. to 220° C., preferably at 90° C. to 180° C. The alkylation reaction may be carried out in inert solvents such as nitromethane, methylene chloride, carbon tetrachloride, dichloroethane, chlorobenzene, dichlorobenzene, nitrobenzene or a combination of these solvents. Other solvents such as benzene, toluene, and xylene may also be used, but the solvents may become alkylated. The product of the reaction of 5,5',6,6',7,7',8,8'-octahydro-2,2'-binaphthol with alcohol varies depending on stoichometry and alkylation reagent used. When tertiary alcohol is used as the alkylating agent, mono alkylated 5,5',6,6',7,7',8,8'-octahydro-2,2'-binaphthols were obtained predominantly, even when several equivalents excess of tertiary alcohol was applied. A large excess of the secondary alcohol (relative to 5,5',6,6',7,7',8,8'-octahydro-2,2'-binaphthol) gave rise to both mono and double alkylated products.

Catalysts used in the processes of the present invention may be unsupported or supported. Suitable supports include silicon dioxide, zeolites, alumino silicates, and polystyrene.

The compounds which are produced by the process of the present invention can be used as reactants to make phosphorous-containing ligands that are useful to make catalysts that, in turn, are useful in both hydrocyanation and hydroformylation reactions. Bidentate phosphite ligands are particularly useful.

Bidentate phosphite ligands can be prepared as described in U.S. Pat. No. 5,235,113 by contacting phosphorochloridites with the compounds made by the processes of the present invention. More recent U.S. Pat. Nos. 6,031,120 and 6,069,267, incorporated herein by reference, describe selective synthesis of bidentate phosphite ligands in which a phosphorochloridite is prepared in-situ from phosphorus trichloride and a phenol such as o-cresol and then treated in the same reaction vessel with an aromatic diol to give the bidentate phosphite ligand. The alkylated products of the processes of the present invention can be substituted for the aromatic diol in the above process.

The compounds made by the processes of the present invention can be used to make polymeric ligands by a process which comprises (1) reacting the compounds made by the processes of the present invention with a benzyl chloride containing polymer, in the presence of a Lewis acid catalyst, and (2) reacting the product of step (1) with at least one phosphorochloridite compound in the presence of an organic base. Preferably the Lewis acid catalyst is zinc chloride or aluminum chloride, and the organic base is a trialkylamine.

Two particularly important industrial catalytic reactions using phosphorus-containing ligands are olefin hydrocyanation and isomerization of branched nitriles to linear nitriles. Phosphite ligands are particularly useful for both reactions. The hydrocyanation of unactivated and activated ethylenically unsaturated compounds (olefins) using transition metal complexes with monodentate and bidentate phosphite ligands is well known. Bidentate phosphinite and phosphonite ligands are useful as part of a catalyst system for the hydrocyanation of ethylenically unsaturated compounds. Bidentate phosphinite ligands are also useful as part of a catalyst system for the hydrocyanation of aromatic vinyl compounds.

Hydroformylation is another industrially useful process that utilizes catalysts made from phosphorus-containing ligands. The use of phosphine ligands, including diphosphines, is known for this purpose. The use of catalysts made from phosphite ligands is also known. Such catalysts usually contain a Group VIII metal. See for example, U.S. Pat. No. 5,235,113, the disclosure of which is incorporated herein by reference.

The present invention also relates to compounds of the formula

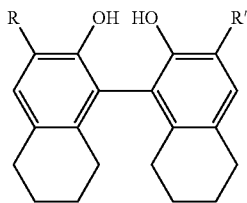

wherein:
R is H; and
R' is ethyl, $C_3$ to $C_6$ secondary, tertiary, or cyclic alkyl;
or a compound of the above formula wherein R and R' are the same and are selected from the group consisting of ethyl, $C_3$ to $C_6$ secondary or cyclic alkyl.
Preferred compounds are those wherein R and R' are the same are selected from the group consisting of ethyl, isopropyl, cyclopentyl, and cyclohexyl.

EXAMPLES

The following non-limiting, representative examples illustrate the processes and compositions of the present invention.

Example 1

Synthesis of 3-isopropyl-5,5',6,6',7,7',8,8'-octahydro-2,2'-binaphthol and 3,3'-diisopropyl-5,5',6,6',7,7',8,8'-octahydro-2,2'-binaphthol A mixture of 5,5',6,6',7,7',8,8'-octahydro-2,2'-binaphthol (30.0 g), xylene (5 ml) and phosphotungstic acid (1.5 g) was heated to 140° C. To the mixture was added propylene (8.9 g) slowly via a dry-ice condenser. GC analysis of the reaction mixture indicated that 98% conversion of the 5,5',6,6',7,7',8,8'-octahydro-2,2'-binaphthol. Small amounts of isopropylated xylene were observed as well. The mixture was purified by flash column to give 14.5 g of 3-isopropyl-5,5',6,6',7,7',8,8'-octahydro-2,2'-binaphthol, mp 110° C.; 3.7 g of 3,3'-diisopropyl-5,5',6,6',7,7'8,8'-octahydro-2,2'-binaphthol, mp 152–3° C.; and a mixture (15 g) containing 38% of 3-isopropyl-5,5',6,6',7,7',8,8'-octahydro-2,2'-binaphthol and 33% of 3,3'-diisopropyl-5,5',6,6',7,7'8,8'-octahydro-2,2'-binaphthol.

3-isopropyl-5,5',6,6',7,7',8,8'-octahydro-2,2'-binaphthol:
$^{13}$C NMR (CDCl$_3$): 22.57, 22.63, 22.96, 23.02, 23.2, 26.9, 27.09, 27.14, 29.3, 29.4, 112.9, 118.4, 119.2, 127.7, 129.5, 130.1, 131.0, 132.5, 133.9, 137.2, 148.7, 151.5 ppm. $^1$H NMR (CDCl$_3$): 1.27 (d, J=7 Hz, 6H), 1.68 (m, 4H), 1.75 (m, 4H), 2.23 (m, 4H), 2.76 (m, 4H), 3.28 (septet, J=7 Hz, 1H), 4.61 (s, 1H), 4.63 (s, 1H), 6.83 (s, 1H), 7.01 (s, 1H), 7.08 (s, 1H) ppm.

3,3'-diisopropyl-5,5',6,6',7,7',8,8'-octahydro-2,2'-binaphthol:
$^1$H NMR (CDCl$_3$): 1.27 (d, J=7 Hz, 12H), 1.68 (m, 4H), 1.73 (m, 4H), 2.17 (AB q & t, J=17, 6 Hz, 4H), 2.78 (t, J=6 Hz, 4H), 3.27 (septet, J=7 Hz, 2H), 4.64 (s, 2H), 6.98 (s, 2H) ppm.

Example 2

Synthesis of 3,3'-diisopropyl-5,5',6,6',7,7',8,8'-octahydro-2,2'-binaphthol

A mixture of 5,5',6,6',7,7',8,8'-octahydro-2,2'-binaphthol (44.0 g), dichlorobenzene (10 ml) and phosphotungstic acid (2.3 g) was heated to 130° C. To the mixture was added excess propylene via a dry-ice condenser. The reaction was monitored by GC analysis. The reaction mixture contained 6% of monoisopropylated product and 83% of diisopropylated product. The mixture was purified by flash column to give 20.0 g of 3,3'-diisopropyl-5,5',6,6',7,7',8,8'-octahydro-2,2'-binaphthol.

Example 3

Synthesis of 3,3'-dicyclopentyl-5,5',6,6',7,7',8,8'-octahydro-2,2'-binapthol

A mixture of 5,5',6,6',7,7',8,8'-octahydro-2,2'-binapthol (48 g), phosphotungstic acid (2.4 g) and cyclopentene (58 g) was charged into a Hastelloy reactor. The reactor was heated to 180 C for 40 hours. The mixture was purified by column chromatography (silica gel, eluting with 2% ethyl acetate/hexane) to yield 29.5 g (42%) of 3,3'-dicyclopentyl-5,5',6,6',7,7',8,8'-octahydro-2,2'-binapthol, mp 143–152° C. $^{13}$C NMR (CDCl$_3$): 22.96, 25.31, 26.68, 29.19, 32.72, 32.75, 39.20, 118.58, 128.14, 129.20, 129.74, 133.91, 149.14 ppm. $^1$H NMR (CDCl$_3$): 1.60 (m, 10H), 2.0 (d, 4H), 2.65 (t, J=4 Hz, 2H), 3.27 (quintet, J=7 Hz, 1H), 4.55 (s, 1H), 6.92 (s, 1H) ppm.

Example 4

Alkylation of 5,5',6,6',7,7',8,8'-octahydro-2,2'-binaphthol with propylene and phosphotungstic acid catalyst A solution of 5,5',6,6',7,7',8,8'-octahydro-2,2'-binapthol in o-dichlorobenzene and dodecane (24 weight % of 5,5',6,6',7,7',8,8'-octahydro-2,2'-binapthol, 63 weight % o-dichlorobenzene, 13 weight % dodecane) was heated to 140° C. for 3 hours under 60 to 70 psi of propylene in the presence of 17 weight % of phosphotungstic acid. GC analysis indicated 100% conversion of 5,5',6,6',7,7',8,8'-octahydro-2,2'-binapthol and formation of 3,3'-diisopropyl-5,5',6,6',7,7',8,8'-octahydro-2,2'-binapthol (55%).

Example 5

Alkylation of 5,5',6,6',7,7',8,8'-octahydro-2,2'-binaphthol with propylene and Amberlyst®15 ion-exchange resin catalyst A solution of 5,5',6,6',7,7',8,8'-octahydro-2,2'-binapthol in o-dichlorobenzene and dodecane (24 weight % of 5,5',6,6',7,7',8,8'-octahydro-2,2'-binapthol, 63 weight % o-dichlorobenzene, 13 weight % dodecane) was heated to 140° C. for 3 hours under 60 to 70 psi of propylene in the presence of 17 weight % of Amberlyst®15 ion-exchange resin purchased from Aldrich (PO Box 355, Milwaukee, Wis. 53201

USA). GC analysis indicated 100% conversion of 5,5',6,6',7,7',8,8'-octahydro-2,2'-binapthol and formation of 3,3'-diisopropyl-5,5',6,6',7,7',8,8'-octahydro-2,2'-binapthol (53%) and 3-isopropyl-5,5',6,6',7,7',8,8'-octahydro-2,2'-binapthol (18%).

Example 6

Alkylation of 5,5',6,6',7,7',8,8'-octahydro-2,2'-binaphthol with propylene and Nafion®/silica catalyst A solution of 5,5',6,6',7,7',8,8'-octahydro-2,2'-binapthol in o-dichlorobenzene and dodecane (24 weight % of 5,5',6,6',7,7',8,8'-octahydro-2,2'-binapthol, 63 weight % o-dichlorobenzene, 13 weight % dodecane) was heated to 140° C. for 3 hours under 60 to 70 psi of propylene in the presence of 17 weight % Nafion®/silica purchased from Engelhard Corp (Nafion® SAC 13, Engelhard Corp. Beachwood, Ohio). GC analysis indicated 100% conversion of 5,5',6,6',7,7',8,8'-octahydro-2,2'-binapthol and formation of 3-isopropyl-5,5',6,6',7,7',8,8'-octahydro-2,2'-binapthol (22%) and of 3,3'-diisopropyl-5,5',6,6',7,7',8,8'-octahydro-2,2'-binapthol (54%).

Example 7

Alkylation of 5,5',6,6',7,7',8,8'-octahydro-2,2'-binaphthol with propylene and trifluoromethanesulfonic acid on silica catalyst A solution of 5,5',6,6',7,7',8,8'-octahydro-2,2'-binapthol in o-dichlorobenzene and dodecane (24 weight % of 5,5',6,6',7,7',8,8'-octahydro-2,2'-binapthol, 63 weight % o-dichlorobenzene, 13 weight % dodecane) was heated to 140° C. for 3 hours under 60 to 70 psi of propylene in the presence of 17 weight % trifluoromethanesulfonic acid on silica purchased from United Catalysts (PO Box 32370, Louisville, Ky. 40232). GC analysis indicated 81% conversion of 5,5',6,6',7,7',8,8'-octahydro-2,2'-binapthol and formation of 3-isopropyl-5,5',6,6',7,7',8,8'-octahydro-2,2'-binapthol (55%) and of 3,3'-diisopropyl-5,5',6,6',7,7',8,8'-octahydro-2,2'-binapthol (25%) based on consumed 5,5',6,6',7,7',8,8'-octahydro-2,2'-binapthol.

Example 8

Alkylation of 5,5',6,6',7,7',8,8'-octahydro-2,2'-binaphthol with propylene and sulfated zirconia catalyst A solution of 5,5',6,6',7,7',8,8'-octahydro-2,2'-binapthol in o-dichlorobenzene and dodecane (24 weight % of 5,5',6,6',7,7',8,8'-octahydro-2,2'-binapthol, 63 weight % o-dichlorobenzene, 13 weight % dodecane) was heated to 140° C. for 3 hours under 60 to 70 psi of propylene in the presence of 17 weight % sulfated zirconia purchased from MEL Chemicals (XZO682/01, MEL Chemicals, Flemington, N.J.). GC analysis indicated 100% conversion of 5,5',6,6',7,7',8,8'-octahydro-2,2'-binapthol and formation of 3-isopropyl-5,5',6,6',7,7',8,8'-octahydro-2,2'-binapthol (5%) and of 3,3'-diisopropyl-5,5',6,6',7,7',8,8'-octahydro-2,2'-binapthol (77%).

Example 9

Alkylation of 5,5',6,6',7,7',8,8'-octahydro-2,2'-binaphthol with propylene and Dowex 32® (ion exchange resin based on sulfonic acids) catalyst A solution of 5,5',6,6',7,7',8,8'-octahydro-2,2'-binapthol in o-dichlorobenzene and dodecane (24 weight % of 5,5',6,6',7,7',8,8'-octahydro-2,2'-binapthol, 63 weight % o-dichlorobenzene, 13 weight % dodecane) was heated to 140° C. for 3 hours under 60 to 70 psi of propylene in the presence of 17 weight % Dowex 32®, Dow No. 8435445, purchased from Dow Chemical (Midland, Mich., USA). GC analysis indicated 100% conversion of 5,5',6,6',7,7',8,8'-octahydro-2,2'-binapthol and formation of 3-isopropyl-5,5',6,6',7,7',8,8'-octahydro-2,2'-binapthol (25%) and of 3,3'-diisopropyl-5,5',6,6',7,7',8,8'-octahydro-2,2'-binapthol (55%).

Example 10

Alkylation of 5,5',6,6',7,7',8,8'-octahydro-2,2'-binaphthol with propylene and Deloxin® ASP (alkylsulfonic acid on silica) catalyst A solution of 5,5',6,6',7,7',8,8'-octahydro-2,2'-binapthol in o-dichlorobenzene and dodecane (24 weight % of 5,5',6,6',7,7',8,8'-octahydro-2,2'-binapthol, 63 weight % o-dichlorobenzene, 13 weight % dodecane) was heated to 140° C. for 3 hours under 60 to 70 psi of propylene in the presence of 17 weight % of Deloxin® ASP (alkylsulfonic acid on silica) produced by Degussa (Hanau, Deutschland). GC analysis indicated 100% conversion of 5,5',6,6',7,7',8,8'-octahydro-2,2'-binapthol and formation of 3-isopropyl-5,5',6,6',7,7',8,8'-octahydro-2,2'-binapthol (63%) and of 3,3'-diisopropyl-5,5',6,6',7,7',8,8'-octahydro-2,2'-binapthol (<10%).

Example 11

Alkylation of 5,5',6,6',7,7',8,8'-octahydro-2,2'-binaphthol with tertiary-butyl chloride and zinc chloride catalyst A mixture of 5,5',6,6',7,7',8,8'-octahydro-2,2'-binapthol (5.0 g), zinc chloride (0.4 g), chloroform (5 ml), and tertiary-butyl chloride (10 g) was heated to 60° C. for 4 hours. GC analysis indicated 90% conversion of 5,5',6,6',7,7',8,8'-octahydro-2,2'-binapthol and formation of 3-t-butyl-5,5',6,6',7,7',8,8'-octahydro-2,2'-binapthol (95%) and of 3,3'-di-t-butyl-5,5',6,6',7,7',8,8'-octahydro-2,2'-binapthol (~2.4%) based on consumed of 5,5',6,6',7,7',8,8'-octahydro-2,2'-binapthol. The mixture was purified by flash column chromatography to yield 4.36 g of solid. $^1$H NMR (CDCl$_3$): 1.43 (s, 9H), 1.65–1.88 (m, 8H), 2.09–2.34 (m, 4H), 2.71–2.79 (m, 4H), 4.66 (s, 1H), 4.87 (s, 1H), 6.82 (d, 1H, J=8 Hz), 7.04 (d, 1H, J=8 Hz), 7.10 (s, 1H) ppm. $^{13}$C NMR (CDCl$_3$): 22.9, 23.0, 23.1, 23.2, 26.8, 27.0, 29.2, 29.4, 29.6, 34.5, 113.0, 119.1, 119.3, 128.2, 128.9, 130.0, 131.0, 133.8, 134.2, 137.2, 149.9, 151.6 ppm.

Example 12

Alkylation of 5,5',6,6',7,7',8,8'-octahydro-2,2'-binaphthol with benzyl alcohol and trifluoromethanesulfonic acid A mixture of 5,5',6,6',7,7',8,8'-octahydro-2,2'-binapthol (1.5 g), trifluoromethanesulfonic (61 mg), o-carbon tetrachloride (2 ml), and benzyl alcohol (0.55 g) was heated to 80° C. for 2.5 hours. GC analysis indicated 73% conversion of 5,5',6,6',7,7',8,8'-octahydro-2,2'-binapthol and formation of 3-benzyl-5,5',6,6',7,7',8,8'-octahydro-2,2'-binapthol (90%) based on consumed of 5,5',6,6',7,7',8,8'-octahydro-2,2'-binapthol. To the cooled reaction mixture was added 10 mL 10% NaOH. The layers were separated, and the aqueous layer was extracted with ethyl aceate. The organic layers were combined, washed with brine, dried and concentrated. The crude material was purified by flash column chromatography (silica gel, eluting with 2% ethyl acetate/hexanes to 5% ethyl acetate/hexanes), to yield 1.13 g white solid (58% yield). $^1$H NMR (CDCl$_3$): 1.56–1.67 (m, 8H), 2.03–2.21 (m, 4H), 2.59–2.67 (m, 4H), 3.93 (s, 2H), 4.47 (s, 1H), 4.56 (s, 1H), 6.72 (d, 1H, J=5 Hz), 6.79 (s, 1H), 6.96 (d, 1H, J=5 Hz), 7.10–7.21 (m, 5H) ppm. $^{13}$C NMR (CDCl$_3$): 22.79, 22.87, 22.91, 26.79, 26.94, 29.00, 29.07, 35.72, 112.78, 118.52, 118.90, 125.02, 125.71, 128.18, 128.68, 129.62, 129.94, 130.83, 131.68, 134.76, 136.96, 140.85, 149.07, 151.23 ppm.

Example 13

Alkylation of 5,5',6,6',7,7',8,8'-octahydro-2,2'-binaphthol with benzyl chloride and zinc chloride catalyst A mixture of 5,5',6,6',7,7',8,8'-octahydro-2,2'-binapthol (0.59 g), zinc chloride (40 mg), chloroform (2 ml), and benzyl chloride (0.27 g) was heated to 60° C. for 4.5 hours. GC analysis indicated 70% conversion of 5,5',6,6',7,7',8,8'-octahydro-2,2'-binapthol and formation of 3-benzyl-5,5',6,6',7,7',8,8'-octahydro-2,2'-binapthol (95%) based on consumed of 5,5',6,6',7,7',8,8'-octahydro-2,2'-binapthol.

Example 14

Synthesis of 3-isopropyl-5,5',6,6',7,7',8,8'-octahydro-2,2'-binaphthol

A mixture of 5,5',6,6',7,7',8,8'-octahydro-2,2'-binaphthol (2 g, 6.8 mmol), isopropyl methanesulfonate (5.5 mmol), scandium triflate (0.34 g, 5 mol %), and carbon tetrachloride (10 ml) was brought to reflux under argon. After 18 hours, GC indicated 65% conversion to give 78% desired product. Additional isopropyl methanesulfonate (3.1 mmol) was added, and the reaction mixture was refluxed for another 8 hours. GC showed 86% conversion, and 76% selectivity to 3-isopropyl-5,5',6,6',7,7',8,8'-octahydro-2,2'-binaphthol. The mixture was diluted with ether (20 ml) and 10% HCl (20 ml). The layers were separated, and the aqueous layer was extracted with ether (3×20 ml). The ether layers were combined, dried (MgSO$_4$), and concentrated. The crude product was purified by column chromatography (SiO$_2$, 2% ethyl acetate/hexanes) to yield 1.1 g white solid (48%). MP: 100–102° C.

Example 15

Synthesis of 3-cyclopentyl-5,5',6,6',7,7',8,8'-octahydro-2,2'-binaphthol

A mixture of 5,5',6,6',7,7',8,8'-octahydro-2,2'-binaphthol (2 g, 6.8 mmol), cyclopentyl methanesulfonate (6.34 mmol), scandium triflate (0.34 g, 5 mol %) and carbon tetrachloride (10 ml) was heated to reflux under argon for 10 hours. GC showed 93% conversion and 77% selectivity to 3-cyclopentyl-5,5',6,6',7,7',8,8'-octahydro-2,2'-binaphthol. The mixture was diluted with ether (20 ml) and 10% HCl (20 ml). The layers were separated, and the aqueous layer was extracted with ether (3×20 ml). The ether layers were combined, dried (MgSO$_4$), and concentrated. The crude product was purified by column chromatography (SiO$_2$, 2% ethyl acetate/hexanes) to yield 1.4 g white solid (57%). $^1$H NMR (CDCl$_3$): 1.58 (m, 14H), 2.05 (m, 6H), 2.66 (m, J=5 Hz, 4H), 3.18 (quintet, J=8 Hz, 1H), 4.52 (s, 1H), 4.51 (s, 1H), 6.73 (d, J=8 Hz, 1H), 6.92 (s, 1H), 6.97 (d, J=8 Hz, 1H) ppm. $^{13}$C NMR (CDCl$_3$): 22.82, 22.87, 23.01, 25.36, 26.70, 26.94, 29.09, 29.20, 32.73, 32.75, 39.28, 112.73, 118.23, 119.13, 128.24, 129.19, 129.85, 130.72, 133.72, 137.03, 149.14, and 151.33 ppm.

Example 16

Synthesis of 3-tert-butyl-5,5',6,6',7,7',8,8'-octahydro-2,2'-binaphthol

A mixture of 5,5',6,6',7,7',8,8'-octahydro-2,2'-binaphthol (1.0 g, 3.4 mmol), tert-butyl alcohol (1.4 g), trifluoromethanesulfonic acid (0.04 g) was dissolved in 2 ml 1,2-dichlorobenzene. The mixture was heated at 120° C. for 2.5 hours. GC showed 97% conversion to 87% mono-butylated product, and 10% bis-butylated product. The mixture was cooled, and diluted with 10 ml water and 10 ml ether. The layers were separated, and the organic layer was washed with sodium bicarbonate solution, dried, and concentrated. The crude product was purified by flash column chromatography (silica gel, 2% ethyl acetate/hexanes) to yield 0.7 g of white solid.

What is claimed is:

1. A process for making 3-alkylated-5,5',6,6',7,7',8,8'-octahydro-2,2'-binaphthol, comprising contacting 5,5',6,6',7,7',8,8'-octahydro-2,2'-binaphthol with at least one alkene or cycloalkene in the presence of an acid catalyst, wherein said acid catalyst is selected from the group consisting of trifluoromethanesulfonic acid on silica and alkylsulfonic acid on silica.

2. The process of claim 1 wherein the at least one alkene or cycloalkene is monoethylenically unsaturated and contains from 3 to 20 carbon atoms.

3. The process of claim 2 wherein at least one alkene or cycloalkene is selected from the group consisting of propylene, butene, pentene, hexene, cyclopentene, and cyclohexene.

4. The process of claim 1 wherein the contacting is done at a temperature between 20° C. and 220° C.

5. The process of claim 4 wherein the temperature is between 90° C. and 180° C. and wherein the 5,5',6,6',7,7',8,8'-octahydro-2,2'-binaphthol is contacted with a mono- or 1,2-disubstituted alkene.

6. The process of claim 4 wherein the temperature is between 40° C. and 90° C. and wherein the 5,5',6,6',7,7',8,8'-octahydro-2,2'-binaphthol is contacted with at least one alkene selected from the group consisting of 1,1-disubstituted alkene, tri-substituted alkene, tetra-substituted alkene or aryl-substituted alkene.

* * * * *